United States Patent [19]

Inoue

[11] Patent Number: 5,277,898
[45] Date of Patent: Jan. 11, 1994

[54] HAIR PROTECTION FILM FOR COLD PERMANENT WAVE TREATMENT

[76] Inventor: Tomio Inoue, 1-14-3, Nakagawara, Yokkaichi shi, Mie-ken, Japan

[21] Appl. No.: 661,869

[22] Filed: Feb. 27, 1991

[30] Foreign Application Priority Data

Aug. 21, 1989 [JP] Japan ................................. 1-214406
Sep. 29, 1989 [JP] Japan ................................. 1-256693

[51] Int. Cl.$^5$ ..................... A61K 7/09; A61K 35/16; A61K 31/715; A61K 31/79
[52] U.S. Cl. ......................................... 424/71; 424/70; 424/78.02; 424/78.05; 424/DIG. 2; 428/497; 428/520; 428/532; 428/500; 428/913
[58] Field of Search ............. 424/70, 71, 78.02, 78.05, 424/78.36, 78.35, 530, 538, 471-472, 481-482; 428/484, 543, 497, 500, 520, 532, 913

[56] References Cited

U.S. PATENT DOCUMENTS

| | | | |
|---|---|---|---|
| 3,837,349 | 9/1974 | Jedzinak et al. | 424/71 |
| 3,958,581 | 5/1976 | Abegg | 132/7 |
| 4,711,775 | 12/1987 | Dittmar et al. | 424/70 |
| 4,900,545 | 2/1990 | Wisotzki et al. | 424/70 |

FOREIGN PATENT DOCUMENTS

| | | |
|---|---|---|
| WO86/00222 | 1/1986 | European Pat. Off. . |
| 0220670 | 5/1987 | European Pat. Off. . |
| 0005807 | 12/1979 | Fed. Rep. of Germany . |

OTHER PUBLICATIONS

Database Derwent WPIL, accesion No. 91-136037 [19], Derwent Publications Ltd., London, GB; JP-A-3 072 413 (Japan Happy K.K.) *Abstract*.
Patents Abstracts of Japan, vol. 11, No. 246 (C-439)[2693], Aug. 11, 1987; & JP-A-62 53 909 (Kurooda Japan K.K.) Sep. 3, 1987.
Chemical Abstracts, vol. 75, No. 2, Jul.12, 1971, p. 265, abstract No. 9852k, Columbus, Ohio, US; E. Pandula et al.: "Effect of additives on the solubility of protective film coatins", & ACTA Pharm. Hung. 1971, 41(2), 58-62 *Abstract*.

*Primary Examiner*—Edward Webman
*Attorney, Agent, or Firm*—Frishauf, Holtz, Goodman & Woodward

[57] ABSTRACT

A hair protection film of the present invention aims at preventing and curing damage to the hair due to cold permanent wave treatment. The hair protection film for cold permanent wave treatment has a "sandwich" or three layer structure with a center layer coated on both sides with a protective layer. The center layer is formed of a film or a thin layer consisting mainly of at least one of "water-soluble natural sugar", "blood plasma", and "substitute blood plasma", or of a film or a thin film obtained by dispersing an extract of corn grains or a concentrate of brewage in polyvinyl alcohol. The protective layer that coats both surfaces is one of an alkali-soluble coating layer, an acid-soluble coating layer and a heat-soluble coating layer.

6 Claims, No Drawings

HAIR PROTECTION FILM FOR COLD PERMANENT WAVE TREATMENT

BACKGROUND OF THE INVENTION

1. Field of the Invention

The present invention relates to a hair protection film for cold permanent wave treatment, which film facilitates winding of the hair around curling rods and prevents bending of the hair.

b 2. Description of the Related Art

A treatment agent used in a widely practiced cold permanent wave treatment consists of a reducing agent (first liquid) of an alkali solution prepared by adding an alkali agent to a main agent of thioglycolate or salts thereof; and an oxidizing agent (second liquid) consisting mainly of a bromate.

The hair is wound around curling rods to a desired style. The first liquid is applied to the hair to swell the hair by the action of the alkali agent contained in the first liquid, thus helping the main agent comprising thioglycolate to permeate the hair. The thioglycolate permeated in the hair cuts, by reduction, cystine bonds of polypeptide (protein) constituting the cortex of hair. The cystine bonds are displaced to fit the hair to the curling rods. Then, the second liquid is applied to the hair, whereby the cut cystine bonds are formed once again in the state wherein the cut bonds have been displaced. Thus, the waves of hair are fixed.

However, the degree of damage of the hair, due to ultraviolet rays, previous cold permanent wave treatments, and the like, increases towards the tip of the hair. In addition, the cuticles covering the surface portion of hair may be peeled and damaged, the cortices of hair under the cuticles and the matrix filled between cortices may be exposed, or the matrix may flow out. The degree of these undesirable conditions increase towards the tip of hair.

Accordingly, if the damaged hair and the less damaged proximal portions of hair and newly grown hair are treated by the first liquid under the same conditions, the damaged hair is considerably affected and further damaged by the first liquid and shrunken owing to lost of moisture.

Using a method involving applying a cold permanent wave treatment to damaged hair, it is known to subject the hair to a pretreatment process, before it is wound around curling rods. In the pretreatment process, a treatment liquid consisting mainly of PPT (polypeptide, which is protein) is applied to the particularly damaged distal portions of hair (about ⅓ from the tip), thereby reducing the strong influence of the first liquid and preventing shrinkage of hair. In addition, in order to wind the hair, wetted with the treatment liquid, around curling rods smoothly and neatly, without bending the tip of hair, the distal portions of hair, before wound around the rods, are wrapped with hair protection films of Japanese paper or nylon films.

Recently, a first liquid of acid solution consisting mainly of thioglycolate or a salt thereof has been developed and substituted for the above-mentioned first liquid of alkali solution. The first liquid of acid solution has been used similarly with the first solution of alkali solution.

In the prior art, the treatment liquid and hair protection films are used to reduce the strong influence of the first liquid for cold permanent wave treatment, thereby preventing shrinkage of hair and facilitating the winding of the hair around the curling rods. However, there are the problems: the cuticles are peeled and damaged, the damaged hair wherein the matrix between cortices has flown out is not recovered, and the damage to hair due to newly applied cold permanent wave treatment is neither prevented nor recovered, as a result of which the degree of damage to hair is aggravated.

Since additional steps are required of applying the treatment liquid to the hair in advance and winding the hair, wetted with this liquid, around the curling rods, the permanent wave treatment process is complicated.

In addition, the first liquid of acid solution is developed and used to lessen the damage due to the first liquid of alkali solution; however, the hair already damaged by the first solution of alkali solution, ultraviolet, etc. is not recovered even if the first liquid of acid solution is used.

SUMMARY OF THE INVENTION

The object of the present invention is to provide a hair protection film capable of solving the above problems in the prior art.

According to an aspect of the present invention, there is provided a hair protection film for cold permanent wave treatment in which the hair is wound around curling rods with use of the hair protection film and is treated with a treatment liquid, said protection film has a major part formed of a film or a thin layer consisting mainly of at least one of "water-soluble natural sugar", "blood plasma", and "substitute blood plasma", and both surfaces of the major part are coated with any one of an alkali-soluble coating layer, an acid-soluble coating layer and a heat-soluble coating layer.

According to another aspect of the invention, there is provided a hair protection film for cold permanent wave treatment, characterized in that a film-like major part of the hair protection film is formed by dispersing "an extract which is obtained from corn grains with use of sulfurous acid water solution" or "50% concentrate of brewage" in polyvinyl alcohol, and both surfaces of the major part are coated with any one of an alkali-soluble coating layer, an acid-soluble coating layer and a heat-soluble coating layer.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

A hair protection film according to the present invention is formed of a film body with a sandwich-like structure wherein alkali-soluble protection layers, acid-soluble protection layers or heat-soluble protection layers are provided on both sides of a major portion of a film or thin film consisting mainly of "water-soluble natural sugar and blood plasma" or "water-soluble natural sugar and substitute blood plasma", or consisting mainly of at least one of "water-soluble natural sugar", "blood plasma" and "substitute blood plasma". Like the above-described conventional treatment process, the protection film is folded to sandwich a lock of hair, or a lock of hair is wound around a curling rod while held by the protection film. Then, the first liquid of the reducing agent consisting mainly of the alkali agent and thioglycolate is applied to the hair. The first liquid cuts, by reduction, cystine bonds of the hair wound around the curling rod, and displaces the cystine bonds thereby fitting the hair on the curling rod. Thus, the hair is subjected to cold permanent wave treatment.

The water-soluble natural sugar may be one or more selected from glucose, dextran and triglycopolysaccharide (Pruran, tradename: a natural polysaccharide produced from starch). The substitute blood plasma is a solution of publicly known "polyvinylpyrrolidone" or "dextran", which is substituted for blood plasma. Of these materials, the major portion of a film with a thickness of 50 μm or a powder thin film is formed. Both sides of the major portion is coated with one of the following films:

* an alkali-soluble layer composed of, for example, a natural alkali-soluble resin of, e.g. AQUIRIS (tradename: manufactured by Gifu Ceramics Kabushiki Kaisha), or a synthetic alkali-soluble polymer of "Aquris", or natural resin "shellac", ("AQUIRIS" is a mixture of a highly functional resin (alkali-soluble resin, reactive resin, water dispersion medium resin) with a resin having controlled molecular structure (Acrylic ester, methacrylic ester, alpha-methyl styrene, styrene-maleic acid derivative, styrene-(meth)acrylic ester, and vinyl acetate-(meth)acrylic ester))
* an acid-soluble layer composed of, for example, an acid-soluble material obtained by subjecting natural resin "shellac" to alkali treatment ("shellac" is a publicly known natural resin obtained by purifying a resin material secreted from an insect called "Coccus lacca"), or a copolymer of styrene and maleic acid, or
* a heat-soluble layer of, for example, a heat-soluble film of SOAFIL (tradename) or SOAPEARL (tradename) (both produced by Mitsubishi Rayon Kabushiki-Kaisha) consisting mainly of natural polysaccharide, which heat-soluble layer is soluble at about 40° to 50° C. for about 10 to 20 minutes.

After the major portion of the film is coated with one of the above films, the major portion is sealed and protected in a liquid-proof manner.

In some cases, proteins of polypeptide, keratin, and the like are added to the major part of the film.

In the hair protection film of the present invention, which has the above composition, the major part consisting mainly of at least one selected from "water-soluble natural sugar", "blood plasma" and "substitute blood plasma", or of an extract from corn grains or brewage is sealed by the alkali-soluble protection film. Thus, when the major part is put in contact with the first liquid or the reducing agent of alkali solution consisting mainly of alkali agent and thioglycolate, the alkali-soluble protection film is dissolved. The water solution of the first liquid penetrates the major part and immediately dissolves the water-soluble natural sugar and blood plasma or substitute blood plasma. Consequently, the first liquid is diluted, and the stimulation to the damage hair due to the first liquid is relaxed. In addition, the alkali agent in the first liquid swells the hair and the thioglycolate cuts cystine bonds of cortices by reduction.

The dissolved water-soluble natural sugar of the major part of the film are excellent in consolidation power, film-forming property, viscosity, and gloss-providing property. The natural sugar also has a high adhesive force and a high water retention characteristic. The blood plasma is an animal protein, contains blood proteins of albumin and globulin and fibrinogen, and has a good adhesive force. The natural sugar and blood plasma has high adaptability to a human body. Thus, the cuticles, which were chemically/physically affected by the thioglycolate and alkali agent when cystine bonds of hair were severed by reduction by the first liquid, are protected by the contained natural sugar and blood plasma having excellent consolidation power, film-forming property, viscosity, and gloss-providing property. The peeling and damage of the cuticles can be effectively prevented, and the cuticles already damaged by ultraviolet, previous cold permanent wave treatment and hair coloring are cured, whereby the function of the cuticles can be maintained or recovered.

The extract from corn grains includes various soluble components:

(a) free amino acids such as aspartic acid, threonine, serine, glutamic acid, proline, glycine, alanine, valine, methionine, isoleucine, leucine, tyrosine, phenylalanine, histidine, lysine, and arginine;

(b) water-soluble vitamins such as thiamine, riboflavin, vitamin $B_6$, niacin, pantothenic acid, inositol, biotin, folic acid, and choline; and (c) lactic acid.

Where the extract includes at least inositol, choline and lactic acid as soluble components, the liquid containing the extract improves the color, gloss, feel and combing smoothness of the hair. In addition, since a condensed extract from brewage contains a large quantity of amino acids, the extract cures the damaged hair.

The lost matrix caused to flow out by the thioglycolate and alkali agent is made up by the natural sugar and blood plasma which is animal protein and has high adaptability to a human body, and the function of the cortices of hair is recovered.

On the other hand, the hair protection film of the present invention can be sealed by the acid-soluble film. When the first liquid of the acid solution is applied, the acid-soluble film is dissolved by the acid solution. Thus, the same function as with the case of using the alkali-soluble film can be performed.

Further, the hair protection film can be provided with the heat-soluble film. When the hair is heated under the above heating, condition by means of steam, hot air, infrared, and the like following the application of the first liquid, the heat-soluble film is dissolved and the main component such as water-soluble natural sugar permeates the hair. Thus, the same function as with the above cases can be obtained.

The properties of the hair, such as color, gloss, feel, combing smoothness, elasticity, hair diameter and strength, after subjected to the cold permanent wave treatment using the hair protection film of the present invention, are improved and the wave shape of the hair is maintained for a long time.

The functional advantage of the hair protection film, which has the major part containing at least the water-soluble natural sugar or the blood plasma or substitute blood plasma, is lower than that of the above-described hair protection film having the major part of "water-soluble natural sugar and blood plasma (substitute blood plasma)", but the former can perform the required function. Specifically, the former can prevent, at least, the development of damage of hair due to the first liquid. In addition, the protection film having the major part to which polyvinyl alcohol has enhanced softness and is easy to use.

Furthermore, since the protection film of this invention has the above functional advantage, the above-described pre-treatment using the pre-treatment liquid at the time of winding the hair around the curling rod is not necessary, and the process for treatment can be simplified with higher efficiency.

EXAMPLES

Examples of the present invention will now be described.

Example A

A major part of a protection film was formed of a water-soluble film to a thickness of about 40 μm. The water-soluble film was prepared by adding blood plasma to triglycopolysaccharide (Pruran, tradename) or a water-soluble polysaccharide obtained from starch. A protection film with a thickness of about 5 μm, formed of Acris (tradename) or a natural alkali soluble resin, is provided on the major part to seal the major part in a water-proof manner. The protection film was used in the cold permanent wave treatment. It was found that the condition of the hair was improved, and the color, gloss, combing smoothness and diameter of the hair were observed fine, compared to that prior to the treatment.

Example B

A major part of a protection film was formed of a water-soluble film obtained by adding a slight amount of polyvinyl alcohol to a main component or glucose. The major part was sealed by an acid-soluble protection film obtained by subjecting a natural resin shellac to alkali treatment. Thus, the protection film was prepared. The protection film was used in the cold permanent wave treatment, as in Example A. It was found that the protection film itself was soft and was easily put on the hair. After the treatment, the condition of the hair was improved, as in Example A.

Example C

Corn grains were put in an 0.1% sufurous acid water solution, and soluble components were extracted. The extraction was carried out for 24 hours at a temperature of 50° C. of the water solution. After the extraction, a solid portion in the water solution was separated, and water was evaporated from the water solution. Thus, the solution was condensed and brought into contact with an ion exchange substance (e.g. ion exchange resin), whereby the solution was refined and the pH of the acid solution was controlled to be 7 to 9. The obtained extract was dispersed in polyvinyl alcohol, thereby forming a film with a thickness of about 30 μm. The major part of the film was sealed in a water-proof manner by a protection film having a thickness of about 5 μm. Thus, the hair protection film was obtained.

The protection film was used in the cold permanent wave treatment, and it was found that the condition of the hair was improved and the color, gloss and combing smoothness of the hair were recovered to the healthy state. In addition, the effect of the protection film lasted for about 40 days to 80 days.

Example D

Brewage was heated and an alcohol component was removed therefrom. The resultant extract was condensed to a density of 50%, and then dispersed in polyvinyl alcohol, as in Example C, thereby obtaining a film. The film was provided with a protection layer; thus, a hair protection film was obtained. The hair protection film was used in the cold permanent treatment. It was found that the condition of the hair was improved such that the lost matrix was made up, the gloss and combing smoothness of the hair were recovered to the healthy state, the weight of the hair increased, and the moisture content of the hair increased to 11% to 13%, as in the healthy hair.

As has been described above, the hair protection film for cold permanent wave treatment, according to the present invention, can prevent the hair from being damaged in the cold permanent wave treatment and maintain and recover the condition of the hair. In contradiction to the general idea that permanent wave treatment causes damage to the hair, the healthy condition of the hair can be maintained and the process for the treatment can be simplified with higher efficiency.

Additional advantages and modifications will readily occur to those skilled in the art. Therefore, the invention in its broader aspects is not limited to the specific details described herein. Accordingly, various modifications may be made without departing from the spirit or scope of the general inventive concept as defined by the appended claims and their equivalents.

What is claimed is:

1. A hair protection film for cold permanent wave treatment, comprising
    a film having a sandwich structure with a center layer and two protective layers, one coated on each side of said center layer;
    said center layer consisting essentially of a water-soluble sugar; blood plasma; a substitute blood plasma selected from the group consisting of dextran and polyvinylpyrrolidone; or a mixture thereof;
    the protective layers consist essentially of (a) an alkali-soluble coating selected from the group consisting of shellac and an alkali-soluble resin formed of a primary repeating unit selected from the group consisting of acrylic ester, methacrylic ester, alpha-methyl styrene, styrene-maleic acid, styrene-(meth-)acrylic ester and vinylacetate-methacrylic ester; or (b) an acid-soluble coating of alkali-treated shellac.

2. The hair protection film of claim 1 wherein said center layer consists essentially of said blood plasma and triglycopolysaccharide.

3. The hair protection film of claim 1 wherein the protective layers consist essentially of the shellac or the alkali treated shellac.

4. The hair protection film of claim 1 wherein the protective layers consist essentially of the acid soluble coating.

5. The hair protection film of claim 1 wherein the protective layers consist essentially of the alkali soluble coating.

6. A hair protection film for cold permanent wave treatment, comprising
    a film having a sandwich structure with a center layer and two protective layers, one coated on each side of said center layer;
    said center layer consisting essentially of a first component and a second component; said first component is polyvinyl alcohol; and said second component is a member selected from the group consisting of a water-soluble sugar; blood plasma; a substitute blood plasma selected from the group consisting of dextran and polyvinylpyrrolidone, and a mixture thereof;

the protective layers consist essentially of (a) an alkali-soluble coating selected from the group consisting of shellac and an alkali-soluble resin formed of a primary repeating unit selected from the group consisting of acrylic ester, methacrylic ester, alpha-methyl styrene, styrene-maleic acid, styrene-(meth)acrylic ester and vinylacetate-methacrylic ester; or (b) an acid-soluble coating of alkali-treated shellac.

* * * * *